United States Patent [19]
Allen et al.

[11] Patent Number: 5,230,338
[45] Date of Patent: Jul. 27, 1993

[54] INTERACTIVE IMAGE-GUIDED SURGICAL SYSTEM FOR DISPLAYING IMAGES CORRESPONDING TO THE PLACEMENT OF A SURGICAL TOOL OR THE LIKE

[76] Inventors: George S. Allen, 628 Westview Ave., Nashville, Tenn. 37205; Robert L. Galloway, Jr., 7736 Indian Springs Dr., Nashville, Tenn. 37221; Robert J. Maciunas, 6320 Chickering Woods La., Nashville, Tenn. 37215; Charles A. Edwards, II, 2316 Erin La., Nashville, Tenn. 37221; Martin R. Zink, 1044 Berwick Trail, Madison, Tenn. 37195

[21] Appl. No.: 873,535

[22] Filed: Apr. 22, 1992

Related U.S. Application Data

[63] Continuation of Ser. No. 433,347, Nov. 8, 1989, abandoned, which is a continuation-in-part of Ser. No. 119,353, Nov. 10, 1987, Pat. No. 4,991,579.

[51] Int. Cl.⁵ .............................................. A61B 6/00
[52] U.S. Cl. ...................................... 128/653; 606/130
[58] Field of Search ..................... 128/653.1; 606/130; 901/2, 15, 41, 47

[56] References Cited

U.S. PATENT DOCUMENTS

| | | | |
|---|---|---|---|
| 4,069,823 | 1/1978 | Isakov et al. | 606/19 |
| 4,545,713 | 10/1985 | Beni | 606/19 |
| 4,583,539 | 4/1986 | Karlin et al. | 606/19 |
| 4,611,247 | 9/1986 | Ishida et al. | 128/653 R |
| 4,638,798 | 1/1987 | Shelden et al. | 128/653 R |
| 4,698,775 | 10/1987 | Koch et al. | 901/47 |
| 4,791,934 | 12/1988 | Brunnett | 128/653 R |
| 4,808,064 | 2/1989 | Bartholet | 901/47 |
| 4,818,173 | 4/1989 | Khusro | 901/47 |
| 4,828,453 | 5/1989 | Martin et al. | 901/15 |
| 4,945,914 | 8/1990 | Allen | 128/653 R |
| 4,998,533 | 3/1991 | Winkelman | 128/653 R |
| 5,050,608 | 9/1991 | Watanabe et al. | 606/130 |

FOREIGN PATENT DOCUMENTS

WO88/09151 1/1988 PCT Int'l Appl.
8907907 9/1989 PCT Int'l Appl. ............ 128/600.03
2212371 7/1989 United Kingdom.

OTHER PUBLICATIONS

J. Cranio-Max.-Fac. Surg. 15 (1987), George Thieme Verlag, Stuttgart, DE, & NY, N.Y.: Calvarial Growth after Linear Craniectomy in Scaphocephaly as Evaluated by X-ray Stereophotogrammetry.

British Journal of Orthodontics, vol. 13, 1986, pp. 151-157, B. Rune et al.: Roentgen Stereometry in the Study of Craniofacial Anomalies—the State of the Art in Sweden.

J. Neurosurg., vol. 60, Jan. 1984, pp. 166-173, Alberius et al.: Roentgen stereophotogrammetric analysis of restricted periods of neurocranial sutures immobilization in rabbits.

J. Neurosurg., vol. 60, Jan. 1984, pp. 158-165, Alberius et al.: Roentgen stereophotogrammetric analysis of neurocranial suturectomy in rabbits.

Acta Anat., vol. 117, 1983, pp. 170-180, S. Karger AG, Basel, Switzerland, Alberius et al.: Roentgen Stereophotogrammetric Analysis of Growth at Cranial Vault Sutures in the Rabbit.

The American Journal of Anatomy, 1983, Alan R. Liss, Inc., vol. 168, pp. 321-330, Alberius et al.: Kinematics of Cranial Vault Growth in Rabbits.

Acta Radiologica Diagnosis, vol. 24, 1983, Fasc. 4, pp. 343, 352, G. Selvik et al.: A Roentgen Stereophotogrammetric System.

American Journal of Orthod., Jun. 1980, vol. 77, No. 6, pp. 643-653, Rune et al.: Movement of maxillary segments after expansion and/or secondary bone grafting in cleft lip and palate: A roentgen stereophotogrammetric study with the aid of metallic implants.

Cleft Palate Journal, Apr. 1980, vol. 17, No. 2, pp. 155-174, Rune et al.: Movement of The Cleft Maxilla in Infants Relative to the Frontal Bone. A Roentgen Stereophotogrammetric Study with the Aid of Metallic Implants.

Dentomaxillofac. Radiol., vol. 8, pp. 5-13, 1979, Rune et al.: Motion of vone segments after surgicalorthodontic correction of craniofacial deformities.

Acta Radiologica Diagnosis, vol. 19, 1978, Fasc. 3, pp. 423-432, Claesson et al.: Roentgen Stereophotogrammetry for Evaluation of Liver Volume and Shape.

Annales Chirurgiae et Gynaecologiae, vol. 67, pp.

82-84, 1978, Trope et al.: Antineoplastic-Drug Effect Evaluated with a New X-Ray Stereophotographic Measurement of the Tumour Volume.
The Anatomical Record, vol. 213, pp. 207-214, 1985 Alberius et al.: Volumetric Changes in the Developing Rabbit Calvarium.
The Journal of Bone and Joint Surgery, vol. 68B, No. 5, Nov. 1986, pp. 770-774, Mjoeberg et al.: Mechanical Loosening of Total Hip Prostheses.
Acta Radiologica Diagnosis, vol. 27, 1986, Fasc. 6, pp. 619-627, Herrlin et al.: Space Orientation of Total Hip Prosthesis—A method for three-dimensional determination.
The Journal of Bone and Joint Surgery, vol. 66A, No. 8, Oct. 1984, pp. 1198-1210, Karrholm et al.: Changes in Tibiofibular Relationships due to Growth Disturbances after Ankle Fractures in Children.
Spine, vol. 14, No. 2, 1989, pp. 162-165, Bengt Sturesson et al.: Movement of the Sacroiliac Joints—a Roentgen Stereophotogrammetric Analysis.
American Journal of Orthod., vol. 81, No. 1, Rune et al., Jan. 1982, pp. 65-70, Rune et al.: Posteroanterior traction in maxillonasal dysplasia (Binder Syndrome).
Clinical Orthopedics and Related Research, No. 191, Dec. 1984, pp. 129-135, Walheim et al.: Mobility of the Pubic Symphysis.
Acta Orthop, Scan., vol. 54, pp. 408-416, Jun. 1983, Ryd et al.: Migration of the Tibial Component in Successful Unicompartmental Knee Arthtoplasty.
8215 Robotics Age, vol. 7, No. 6, Jun. 1985 pp. 17-22, Peterborough, New Hampshire, US; Y. Kwoh et al.: A new computerized tomographic-aided robotic stereotaxis system .

*Primary Examiner*—Ruth S. Smith
*Attorney, Agent, or Firm*—Kenyon & Kenyon

[57] ABSTRACT

An interactive system for guiding the use of a surgical tool uses at least one imaging technique, such as CT scanning. A mechanical arm has a fixed base at a first end and a tool holder that holds the surgical tool at a second end. A display displays one or more images from the image space of a patient's anatomy. A computer is coupled to the display and the mechanical arm. The computer tracks the location of the surgical tool through physical space, performs a transforming rotation of the physical space to the image space, and causes the display to display the location of the surgical tool within the image space.

24 Claims, 12 Drawing Sheets

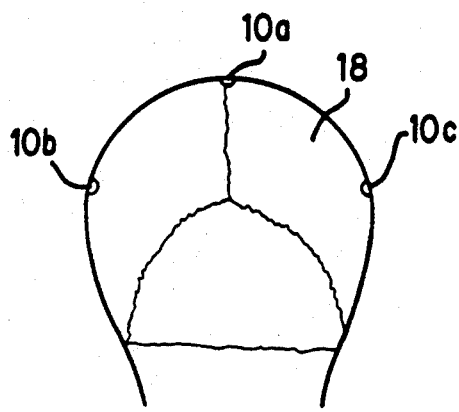
FIG. 1a
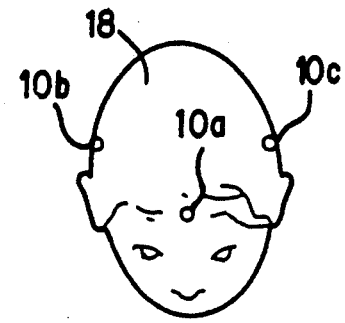
FIG. 1b
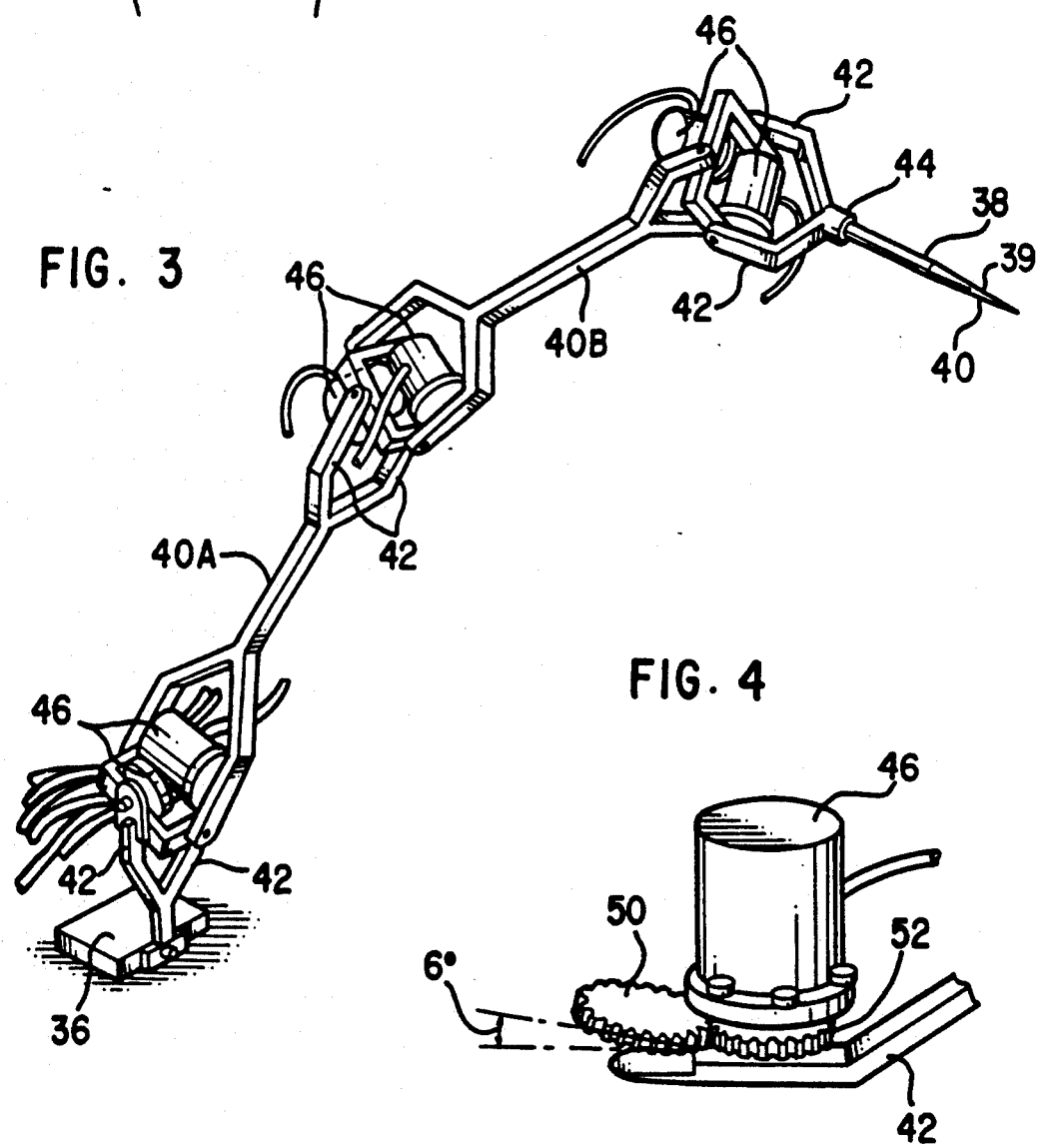
FIG. 3
FIG. 4

INTERACTIVE IMAGE-GUIDED SURGICAL SYSTEM FOR DISPLAYING IMAGES CORRESPONDING TO THE PLACEMENT OF A SURGICAL TOOL OR THE LIKE

This application is a continuation of application Ser. No. 07/433,347, filed on Nov. 8, 1989, now abandoned, which is a continuation-in-part of U.S. Ser. No. 07/119,353 of Nov. 10, 1987, now U.S. Pat. No. 4,881,579.

FIELD OF THE INVENTION

The present invention relates to a system for guiding a surgeon interactively through a surgical procedure, and more particularly to an integrated system of hardware and software which allows for the intuitive use of imaging-derived data regarding a patient's anatomy in order to guide a surgeon through a surgical procedure.

BACKGROUND OF THE INVENTION

There are a number of well-known diagnostic imaging techniques that allow a physician to obtain high fidelity views of the human body. Imaging systems which provide cross-sectional (tomographic) views of anatomical structure without invasive procedures include computed tomography (CT) x-ray imagers and magnetic resonance (MR) imagers.

A problem associated with the scanning techniques is that each imaging process is sensitive to the patient's position within the imaging device. Therefore, each set of images has a discrete, unique orientation. Thus, images formed from the same modality at different times and images formed at essentially the same time, but from different imaging modalities (for example, CT and MRI) cannot be compared on a point-by-point basis. This prevents accurate comparison of regions within the images.

A surgeon also deals with orientation differences to the imaging space. For example, although a neurosurgeon will know where his surgical tool is with regards to certain anatomic landmarks he may not know with the desired precision where the tool is with regards to the lesion visible on the images. There have been attempts to solve this problem by temporary attachment of a relatively large brace-like structure surgically attached to portions of the body, such as the head. By orienting a surgical tool with respect to this structure, and by knowing the location of internal anatomical areas of interest with relation to this attached structure, the position of the surgical tool with respect to the anatomical areas of interest will be known.

A problem with these structures is their size and their interference with normal daily activities, such as sleeping. The structures are therefore not used over a long period of time (e.g. for more than 12 hours) so that a comparison of images, or the location of a specific point within the anatomy, taken over a substantial time period is not practical.

There is therefore a need for an interactive system which will guide a surgeon in the manipulation of a surgical tool to an exact location that is specified by an imaging system.

SUMMARY OF THE INVENTION

This and other needs are satisfied by the present invention which provides an arrangement for an interactive image-guided surgical system. The system according to the present invention defines an internal coordinate system within the anatomy of a patient. The internal coordinate system is located with respect to an external coordinate system, for example, by locating the end tip of a surgical tool with a known reference point in the internal coordinate system. Once the position of the internal coordinate system is known with respect to the external coordinate system, the surgical tool can be moved anywhere within either the external or internal coordinate systems and its location will be known with a high amount of precision.

The present invention also relates to an arm that a surgical tool is attached to for use in an image-guided system. The arm carries position encoders so that as the arm is moved, the location of the surgical tool that is attached to the arm will always be known with respect to the internal coordinate system.

BRIEF DESCRIPTION OF THE DRAWINGS

FIGS. 1A and 1B illustrate different views of a head having fiducial implants located in the head.

FIG. 3 shows a mechanical arm constructed in accordance with an embodiment of the present invention.

FIG. 4 shows an enlarged view of gear engagement for an optical encoder used with the arm of FIG. 3.

DETAILED DESCRIPTION

Figure 2:
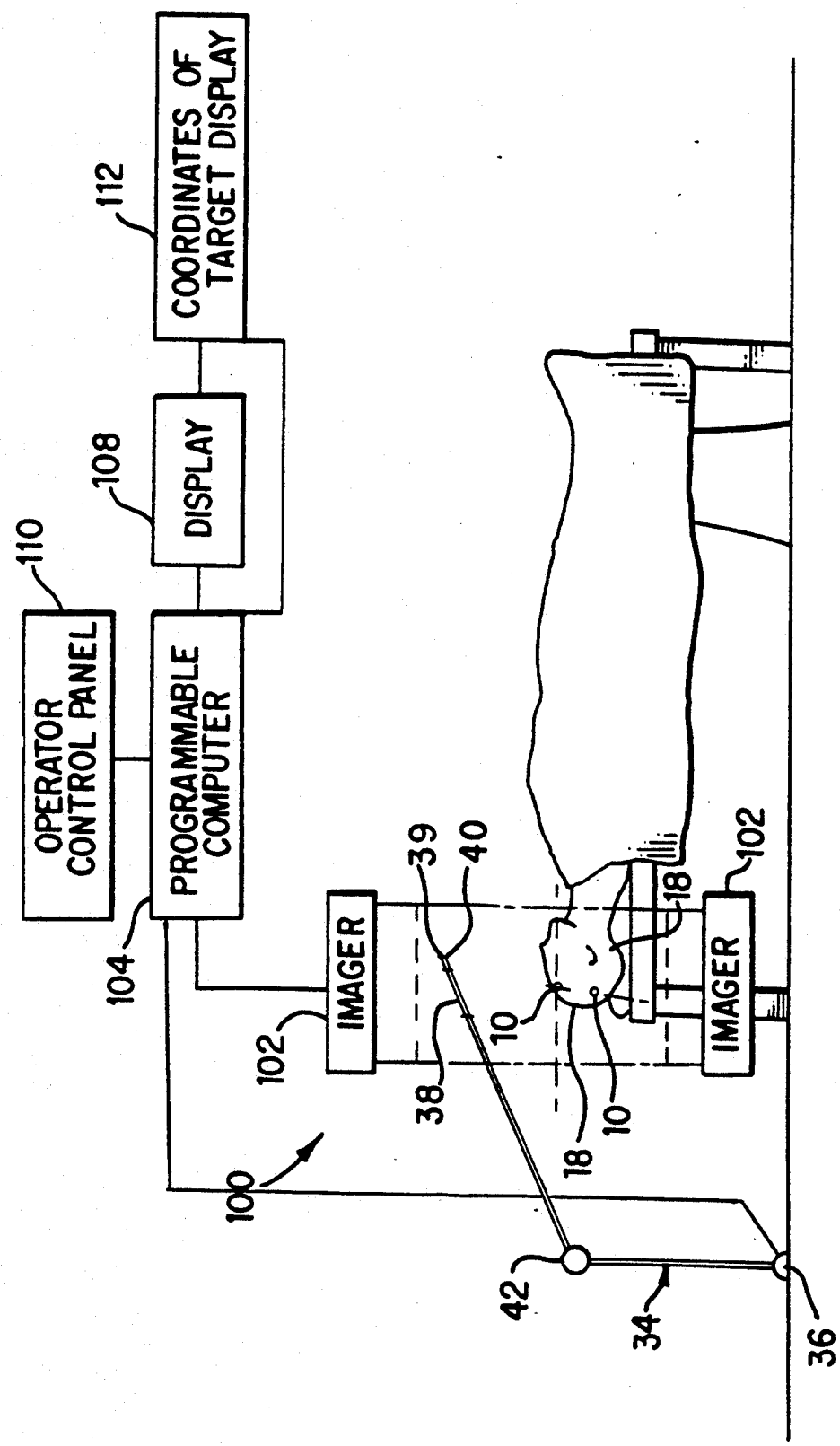
FIG. 2 shows an operating arrangement in accordance with an embodiment of the present invention.

The present invention defines a three-dimensional internal coordinate system that is fixed within a human anatomy. The internal coordinate system is established within the anatomy using the present invention by affixing three or more fiducial implants to portions of the anatomy. The fiducial implants are affixed to points which will not change their spatial relationship to one another over a relatively long period of time, such as a few months.

An example of placement of fiducial implants in the anatomy are shown in FIGS. 1A and 1B. In these drawings, fiducial implants 10A, 10B, 10C are implanted in three separate, spaced locations within a skull 18.

Since these three fiducial implants 10A-C are arranged in a noncollinear manner, a plane is formed which contains these fiducial implants 10A-C. Once a plane is defined, a three-dimensional coordinate system is defined. Any point within the body will be within the internal coordinate system.

Although fiducial implants are shown, any three points that are affixed with respect to the region of interest can comprise the three points used to define the internal coordinate system. However, fiducial implants 10A-C that are identifiable and measurable by different imaging systems, such as CT imagers and MRI imagers, are preferred. The fiducial implants 10A-C can be relatively small and unobtrusive so that no discomfort or self-consciousness will be experienced by the patient even though the patient may carry the implants 10A-C for a relatively long period of time.

A scan, using a known imaging technique, is performed once a patient has the three fiducial implants 10A-C implanted. An internal coordinate system will then be defined with respect to these three fiducial implants 10A-C. During subsequent scans, whether after a few minutes or a few months, the patient's orientation may change relative to the imaging apparatus. However, using the present invention, this new orientation can be measured by locating the fiducial implants 10A-C in relation to the imaging apparatus and comparing their locations to the previously recorded locations. This comparison technique permits re-orienting images of subsequent scans to a position corresponding to the earlier recorded scan so that equivalent image slices can be compared.

Regardless of the reason why the patient is oriented differently, by taking advantage of the fixed, fully-defined internal coordinate system in the anatomy, the location and direction of the plane defined by the three fiducial implants 10A-C in the first imaging session can be compared with the location and direction of the same plane defined by the three fiducial implants at the time of the second imaging session. The cartesian systems are aligned by three independent rotations. The translation of one cartesian coordinate system to another is a well-known technique and readily performable by modern computers. An example of an arrangement which defines an internal coordinate system for the anatomy and performs a transformation with respect to rotation from one cartesian coordinate system to another is described in U.S. patent application 119,353 filed on Nov. 10, 1987 for a "Method and Apparatus for Imaging the Anatomy", and is herein expressly incorporated by reference.

Once the internal coordinate system is established, an external coordinate system is also thereby established by the three noncollinear fiducial implants 10A-C. In order to keep track of a moving point in both the internal and the external coordinate systems, it is merely necessary for the system to initially establish the location of that point with respect to a point in the internal coordinate system and then continuously follow the movement of the point in the external coordinate system. As an example, assume that the point in the external coordinate system is the end tip of a laser. In order to keep track of the location of that end tip in both the external and internal coordinate systems, the end tip of the laser is first brought into a known relationship with one of the fiducial implants 10A-C, for example touching the implant, and the computer notes this initialization. The computer used with the imaging system then follows the location of the end tip as the laser is moved anywhere within the internal and external coordinate systems. A positioning encoder tracks the position of the end tip and feeds signals relating the movement of the end tip within the coordinate systems to the computer. Since the original position of the end tip (i.e. against the fiducial implant 10A-C) is known, and its movements have been continuously tracked and fed to the computer since the original position of the end tip was entered into the computer, the position of the end tip in either the internal or external coordinate systems will be known at all times.

FIG. 2 shows a schematic illustration of an operating environment according to an embodiment of the present invention. In this figure, a patient has fiducial implants 10 A-C implanted in the skull 18. An imager 102 operates as described earlier in conjunction with a programmable computer 104. An operator control panel 11? is coupled to the programmable computer 104, as is a display 108 which includes a target display 112 that displays the coordinates of a target (used in radiation therapy applications).

An external arm 34 is fixed to a base 36. The arm 34 carries a tool 38 which is changeable, and can be for example, a laser or any of a number of surgical tools, such as a pointer, ultrasound unit, biopsy probe, radiation beam collimator, etc. The arm 34 has a number of joints 42, although only one is shown for purposes of illustration in FIG. 2. The movement of the arm 34 is tracked by computer 104 so that the position of the tool 38 relative to the base 36 of the arm 34 will always be known. The movement of the tool 38 through the external and internal coordinate systems (with reference to the base 36 of the external coordinate system) will be known precisely using the following method.

At the end tip 39 of the tool 38 a sensor 40 may be located. The sensor 40 can be a metal detector or an ultrasonic detector, or any instrument that can sense the position of a fiducial implant 10 A-C in the patient. If the fiducial implants 10 A-C are placed in the skull 18, the sensor 40 at the end tip 39 of the tool 38 is moved by the arm 34, under the guidance of the surgeon, until it contacts a fiducial implant 10 in the skull 18. This contact of the end tip 39 with the fiducial implant 10 is noted by the computer so that the initial position of the end tip 39 relative to the internal coordinate system is known. Furthermore, since the position of the end tip 39 relative to the base 36 in the external coordinate system is also always tracked and known, the position of the end tip 39 can be followed through both external and internal coordinate systems following the initialization of placing the end tip 39 into contact with the fiducial implant 10.

The means to track the arm 34 is well known and is accomplished by sensors (not shown in FIG. 2) in various locations of the arm 34, detecting either rotation or movement of the joints 42 of the arm 34.

In surgery, the internal coordinate system defined by the three fiducial implants 10A-C allow, for example, a laser to be followed as it cuts through tissue to a tumor. The imaging system 102 used in the imaging procedure is positioned to continually take imaging data that is provided to the computer 104 and the display 108 to guide the surgeon who manipulates the arm 34 and the laser used as the surgical tool 38. As the laser cuts through the tissue, the change in the tissue will be apparent in the display 10 of imaging system and can be followed with respect to the fixed internal coordinate system.

An example of a mechanical arm whose movements can be tracked and which can hold a variety of surgical tools 38 is shown in FIG. 3. The base 36 of the arm 34 is movably fixed to some location. The arm 34 has two arm links 40A,40B. The first arm link 40A is coupled to the base by two gimbal joints 42. The first arm link 40A therefore has two degrees of motion, as provided by the two gimbal joints 42.

A second arm link 40B is coupled to the first arm link 40A by a second pair of gimbal joints 42. This second pair of gimbal joints 42 provides the second arm link 40B with two additional degrees of motion. Relative to the base 36 of the arm 34, the second arm link 40B therefore has four degrees of motion.

A tool holder 44 is coupled to the second arm link 40B through a pair of gimbal joints 42. The tool holder 44 can hold any of a number of different tools, including a pointer, an ultrasound unit, a surgical laser, a biopsy probe, a radiation beam collimator, etc. The third pair of gimbal joints 42 provides the tool 38 with two additional degrees of motion, so that relative to the base 36, the tool 38 has six degrees of motion.

The exact positioning of the tool 38 relative to the base 36 is kept track of by optical encoders 46. One optical encoder 46 is assigned to each gimbal joint 42. As an individual gimbal joint 42 is rotated around its pivot, the optical encoder 46 determines the precise amount of rotation of the gimbal joint 42 around its pivot. The information from each of the six optical encoders 46 is provided to the programmable computer 104, which can therefore precisely track the movement of the tool 38 relative to the base 36 by keeping track of the individual rotations of the gimbal joints 42 around their pivots.

As can be seen in the embodiment of FIG. 3, the optical encoders 46 are of a size such that they can be arranged within the gimbal joint 42. This makes for a very compact arm structure and accurate encoding of the position of the gimbal joint 42. The entire arm structure 34 is sterilizable and can be made out of stainless steel, for example. Furthermore, in order to make the arm 34 easy to manipulate and use, the arm 34 is counterbalanced in a conventional manner.

Although other means of measuring and feeding back information as to the pivoting or tilting of the gimbal joints 42 can be used, an optical encoder such as commercially available and produced by Heidenhain or by ITEK are suitable. As mentioned before, it is advantageous that the optical encoders 46 are of a size that fits within the gimbal joints.

A detail of the mounting of an optical encoder 46 is shown in FIG. 4. A gear 50 that is coupled to the gimbal joint 42 meshes at an angle of approximate 6° to the gear 52 that drives the optical encoder 46. This angled meshing prevents backlash of the gears so that the accuracy of the readout of the optical encoder is ensured.

During an operation, three separate raster images and a graphic image are displayed on the video display 108 simultaneously to assure the surgeon of accurate spatial orientation. Each different raster image can be supplied by a different type of imaging technology. For example, the three different raster images supplied simultaneously on the video display screen 108 can be from three different imaging modalities such as CT, MRI, etc. Alternatively, multiple slices from a single imaging modality can be displayed simultaneously instead of the same slice from different imaging modalities. A feature of the present invention provides that the displaying of the images is performed in real-time, so that the image slices change as the surgeon moves the arm 34 during surgery.

Although the arm 34 has been described as being usable with the fiducial implants 10A-C, the arm 34 also can be used with other existing stereotactic localization systems and frames, as long as an internal reference point is identifiable. As mentioned earlier, an identifiable internal reference point is used in order to orient the arm 34 in the internal and external coordinate systems.

Figure 5:
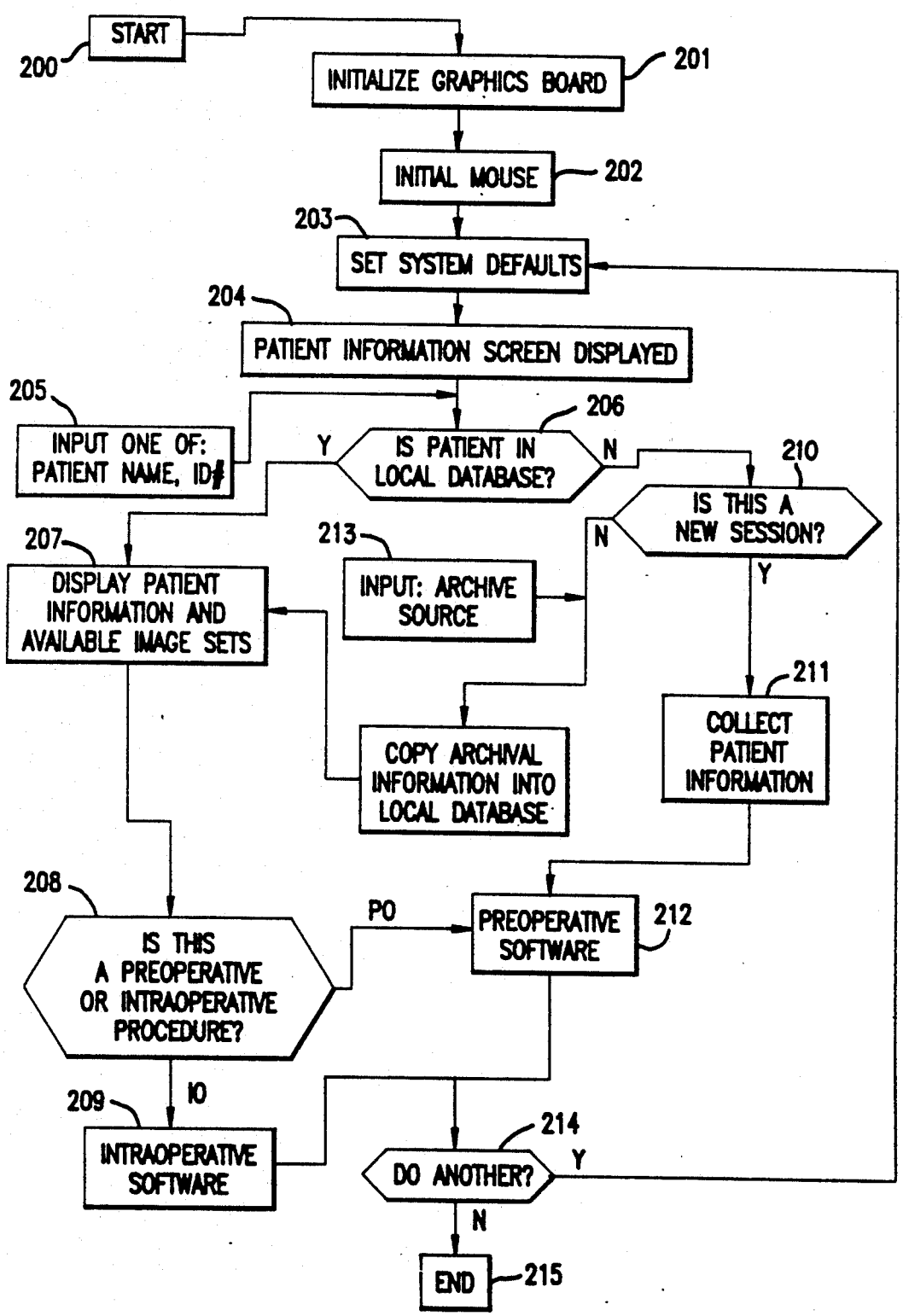
FIG. 5 is a flow chart for an interactive, image-guided surgical system in accordance with an embodiment of the present invention.

FIGS. 5-16 show various flow charts of the software used in the system of the present invention. The first software flowchart is shown in FIG. 5 and depicts an interactive, image-guided surgical system's main program. The main program begins at start 200 and the graphics board is initialized in step 201. The mouse is initialized in step 202 and the system defaults are set in step 203. The patient information is displayed on a screen in step 204 and inputs are provided relating to the patient including the patient name, and ID number in step 205.

In the decision step 206, it is determined whether the patient is in the local database. If the patient is in the local database, the patient information and available image sets are displayed in step 207. At that point, it is determined (step 208) whether the procedure is the preoperative of intraoperative procedure. If it is an intraoperative procedure, the intraoperative software is utilized in step 209.

If the patient is not in the local database, it is determined in decision step 210 whether this is a new session or not. If it is a new session, the patient information is collected (step 211) and the preoperative software is utilized in step 212. If the session is an old session, archival information is input (step 213) and the archival information is copied into a local database. The program proceeds from step 207 in which the patient information and available image sets are displayed. From the preoperative software 212 and the intraoperative software 209 a decision step 214 is entered in which it is decided whether or not to process another patient. If this session is to be ended, step 215 is entered to end the session. If another patient is to be processed, the procedure loops back to set system defaults step 203.

The preoperative software of step 212 comprises six major functions. Image slices that depict a surgical volume of interest are transferred to the system hard disk. This involves either directly reading them from the storage media or by transfer from software. Another function is the displaying of the raster images on the display 108. The third function is the reviewing of the raster data by position to set separate threshold and contrast values for all raster images. Once the raster data is in place, a graphic representation of the raster data is generated in the fourth function. This representation can be wire-framed or shaded surface or both. The fifth function of the preoperative software is the editing of the graphic representation of the raster region. Finally, the physician in the sixth function may chose to mark regions of interest on the raster images. These regions are then transferred into the graphic image set. The flow charts relating to these six functions are shown in FIGS. 6-11.

Figure 6:
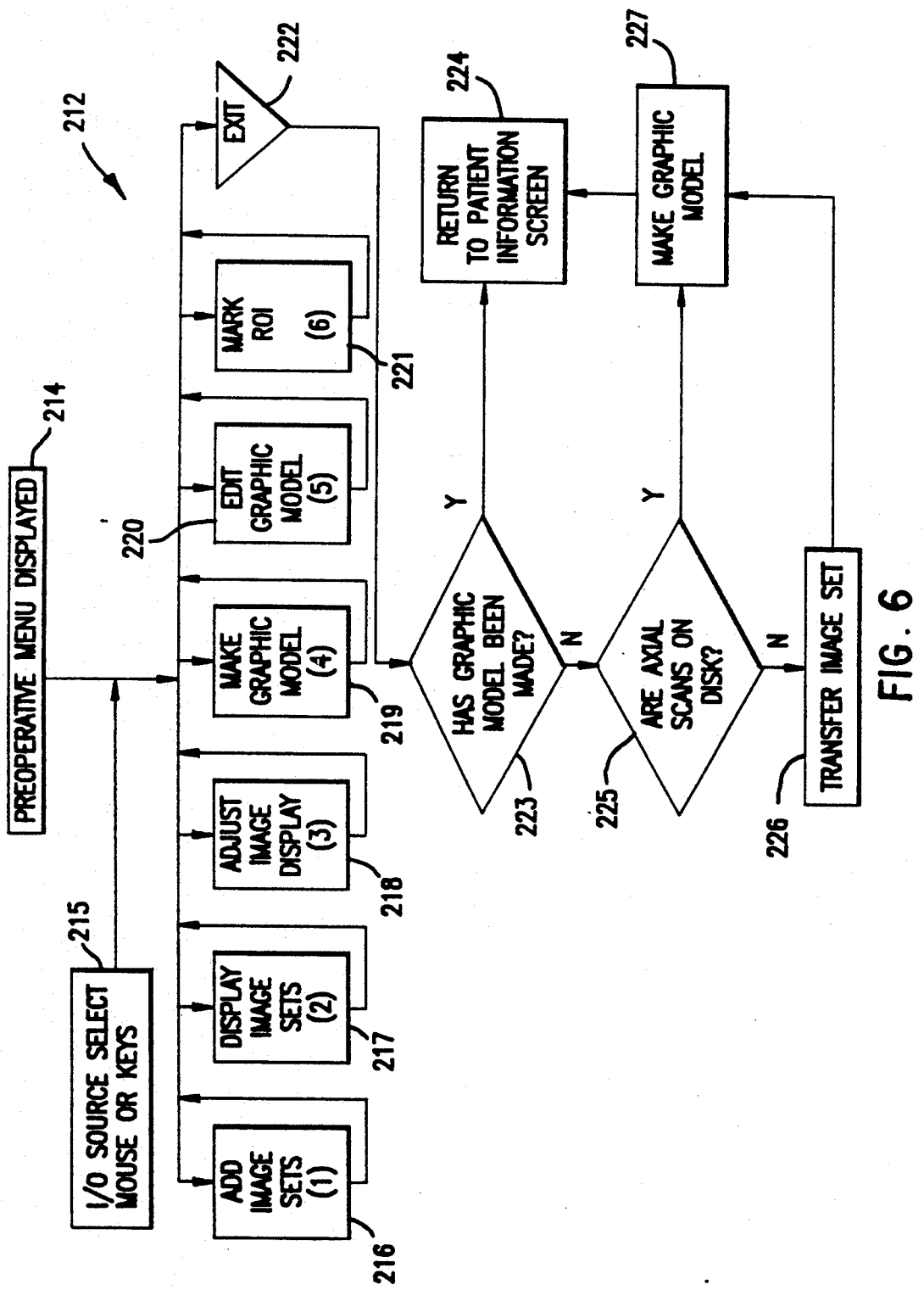
FIG. 6 is a flow chart of the pre-operative software.

FIG. 6 shows the overall flow chart of the preoperative software 212. The first step of the preoperative software 212 is the displaying of the preoperative menu. The I/O source is selected between using a mouse or keys in step 215. From the menu, one of the six functions 216-221 are chosen and performed, or the exit 222 is selected from the menu. From the exit 222 of the menu, it is determined in decision step 223 whether a graphic model has been made. If so, there is a return 224 to the patient information screen on the display 108. If no graphic model has been made, it is next determined in decision step 225 whether actual scans are on the disk. If they are not, the image set is transferred in step 226. If the actual scans are on the disk, a graphic model is made in step 227 and the patient information screen is returned to.

Figure 7:
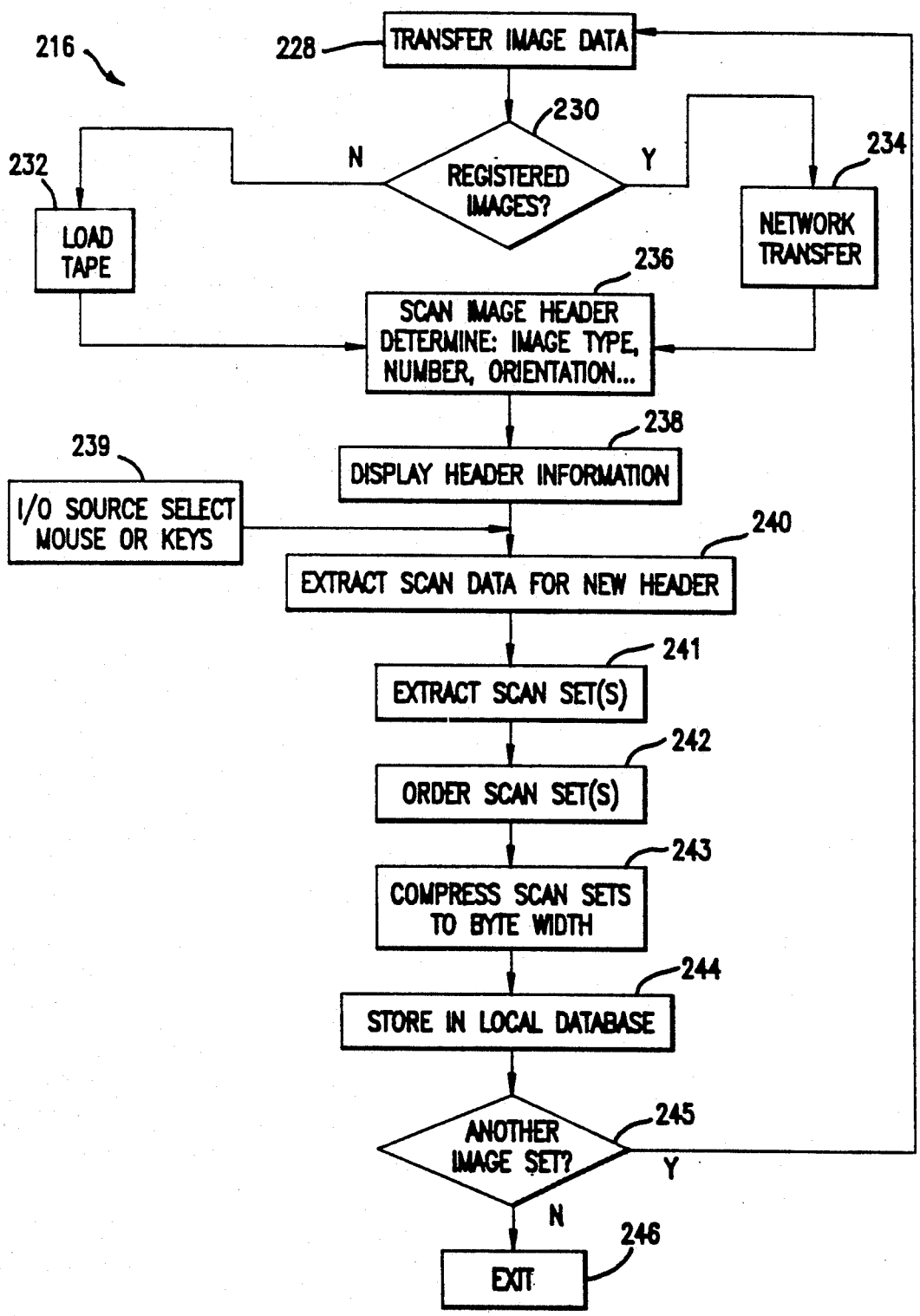
FIG. 7 is a flow chart of the first function of the pre-operative software.

FIG. 7 illustrates the flow chart for the first function, the step of adding image sets 216. In step 228, the image data is transferred. In decision step 230, it is determined whether the images are registered. If they are not registered, a storage tape is loaded (step 232) and if the images are registered, a network transfer is performed in step 234. From either step 232 or 234, an image header is scanned in step 236 to determine the image type, the number, the orientation etc. The header information is displayed on display 108 in step 238. In step 239, the I/O source is selected between mouse or keys. In step 240, the scanned data for the new header is extracted. Scan sets are extracted in step 241, these scanned sets being ordered in step 242. The scanned sets are compressed to byte width in step 243 and are stored in a local database in step 244. In step 245 a decision is made whether to operate on another image set at which time the first function 216 is either exited 246 or returned back to step 228.

Figure 8:
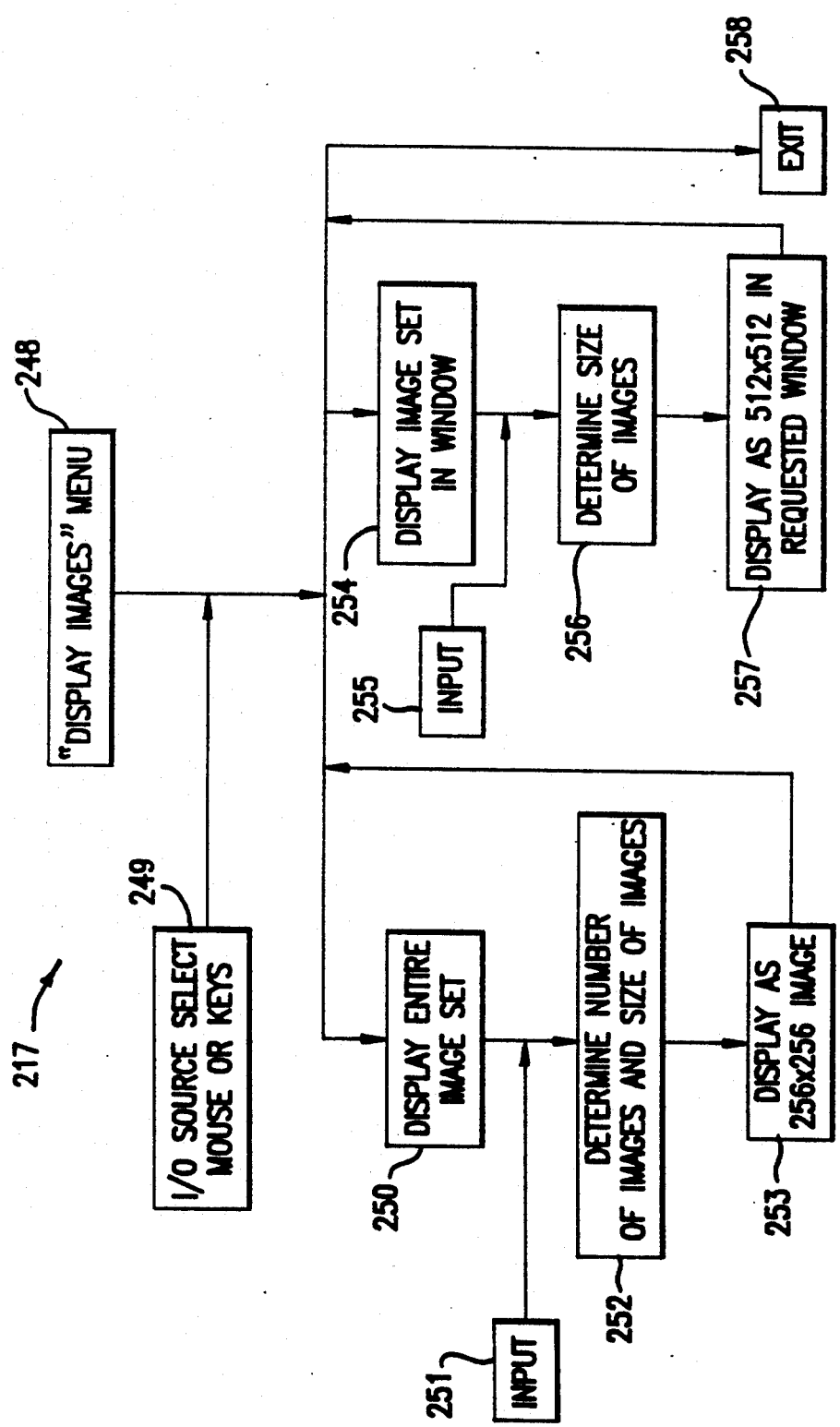
FIG. 8 is a flow chart of the second function of the pre-operative software.

FIG. 8 shows the second function in the preoperative software, the display image set function 217. The first step of this second function is the provision of the menu to display images in step 248. The I/O source is selected in step 249. The entire image set can be displayed in step 250 and with input 251, the number of images and size of the images is determined in step 252. A display with a 256×256 image is displayed in step 253. Alternatively, instead of displaying the entire image set in step 250, the image set can be displayed in a window in step 254. Based upon input in step 255, the size of the images is determined in step 256 and the display can be a 512×512 in a requested window in step 257. The second function of displaying image sets 217 is exited in step 258.

Figure 9:
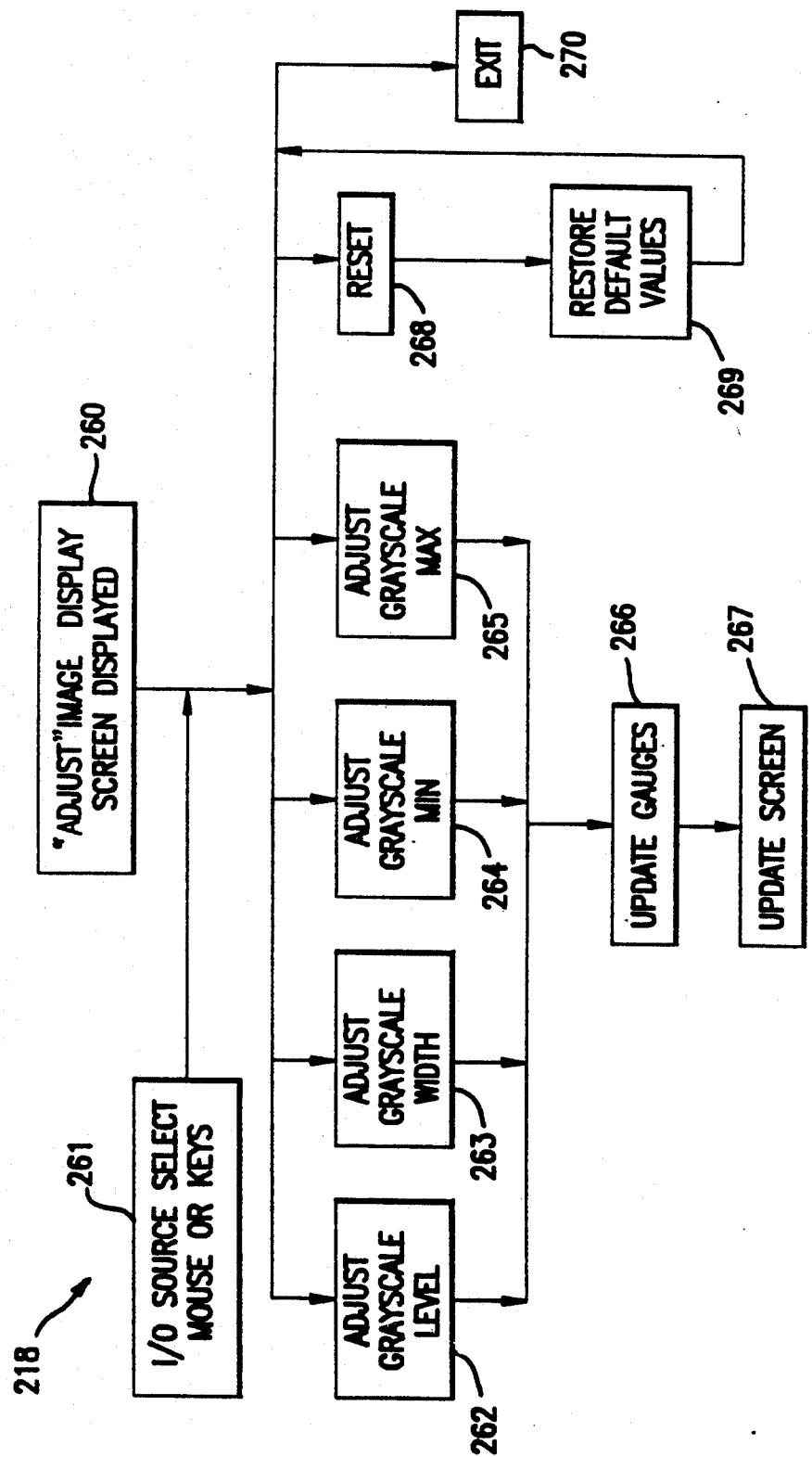
FIG. 9 is a flow chart of a third function of the pre-operative software.

FIG. 9 shows a flow chart of the third function, the adjust image display function 218. Step 260 displays the adjust image menu and step 261 selects the I/O source. From the menu, the level, width, minimum and maximum of the gray scale can be adjusted in steps 262-265. After adjustment, gauges are updated in step 266 and the screen is updated in step 267 with a return to the menu. Also from the menu, there is a reset step 268 that can be chosen to restore default values in step 269. Finally, from the menu, there is an exit 270 from the adjust image display function 218.

Figure 10:
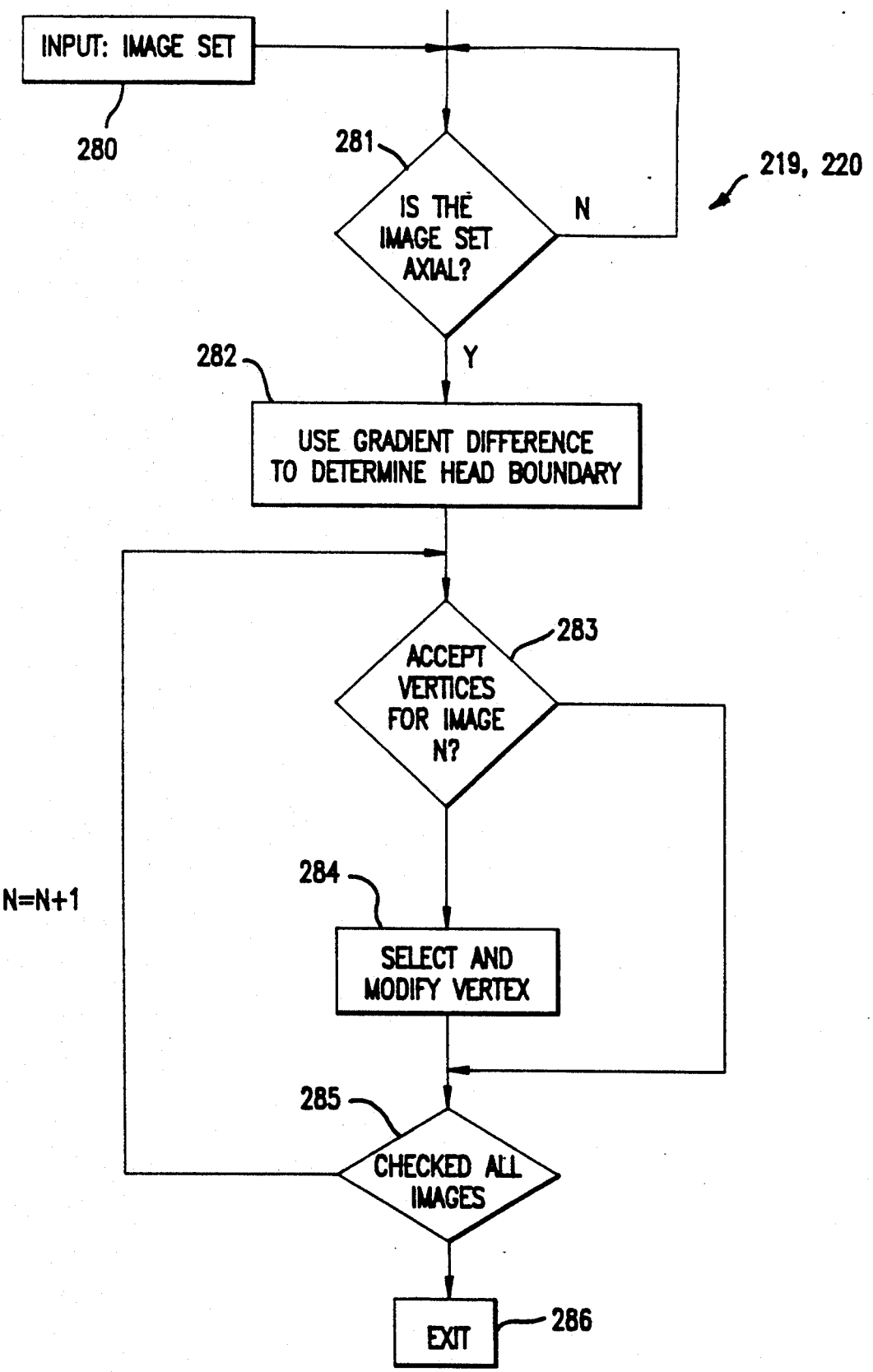
FIG. 10 is a flow chart of the fourth and fifth functions of the pre-operative software.

FIG. 10 illustrates a flow chart for the fourth and fifth functions, the making and editing of the graphic model. In step 280, an image set is input. It is determined in step 281 whether the image set is axial or not. If it is not, there is a loop until the image set is axial. When the image set is axial, the gradient difference is used to determine the boundary of the anatomy of interest, for example the patient's head. In decision step 283, it is determined whether to accept vertices for the image N. If the vertices are not accepted, a vertex is selected and modified in step 284, otherwise, this step 284 is skipped to decision step 285 in which all the images are checked.

The image is then incremented to N=N+1 and the flow loops back to the input of decision step 283 if all the images are not checked. Otherwise, when all the images are checked as determined in decision step 285, the fourth and fifth functions 219, 220 are exited in step 286.

Figure 11:
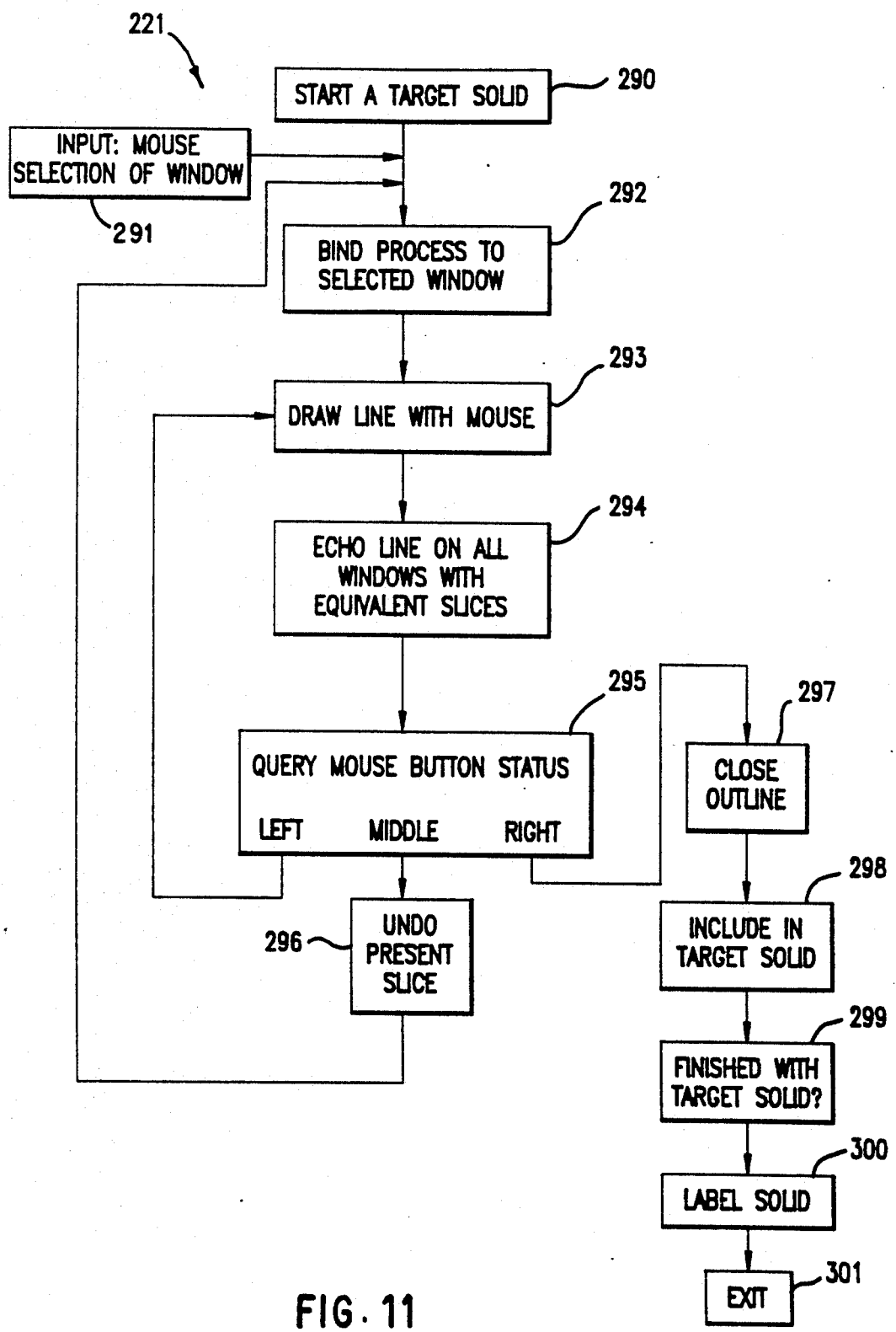
FIG. 11 is a flow chart of the sixth function of the pre-operative software.

The sixth function, the marking of the region 221 is shown as a flow chart in FIG. 11. In 290, a target solid is started. Step 291 involves the selection of a window as an input to the software. The process is binded to the selected window in step 292 and a line is drawn with the mouse in step 293. The line is encoded in step 294 with all the windows having equivalent slices. The input mouse button status is determined in step 295. If the left button is selected, there is a loop back to decision step 293. If the middle button is selected the process loops back to the input step 292. Finally, if the right button is selected, the outline is closed in step 297 and the target solid is included in step 298. It is determined in step 299 whether the target solid is finished, at which time, the solid is labeled in step 300 and the process exited in step 301.

The above procedures and flow charts in FIGS. 6-11 describe the preoperative software 212. The following flow charts describe the intraoperative software 209. The intraoperative software 209 performs several intraoperative tasks and a true intraprocedural task. The intraoperative tasks include confirming the patient data and setting up the computer and surgical device for a specific surgical procedure. The software is checked for resets of the optical encoders after start-up. This ensures accurate angular determination and surgical tool end point positioning. The system display setting for brightness and contrast are changed to maximize image perception within the operating room. The graphic display position is rotatable to the position which is most intuitive to the surgeon. The end tool is also touched to a series of points on a calibration device in order to determine angular errors in each degree of freedom.

The tasks that are performed by the system during the operation are the following. After the patient is positioned, points of commonality between physical space and the image space as seen in the display 108 are sequentially located. A matrix of rotation between the physical space and the image space is calculated The pointer is then moved to any position of interest within the surgical space. The value of each angular encoder is read by the computer 104, the position of the end point 39 of the surgical tool 38 is calculated in the physical space and then transformed by the matrix of rotation to its equivalent position in the image space. This point is shown simultaneously on all the raster windows and in the graphic window Additionally, the position of the distal joint is calculated and shown on the graphic windows to aid the surgeon in orientation. Finally, the surgeon may switch to a display of the trajectory of the tool 38. This allows the surgeon to determine an optimal path to a point of interest within the surgical or image space.

Figure 12:
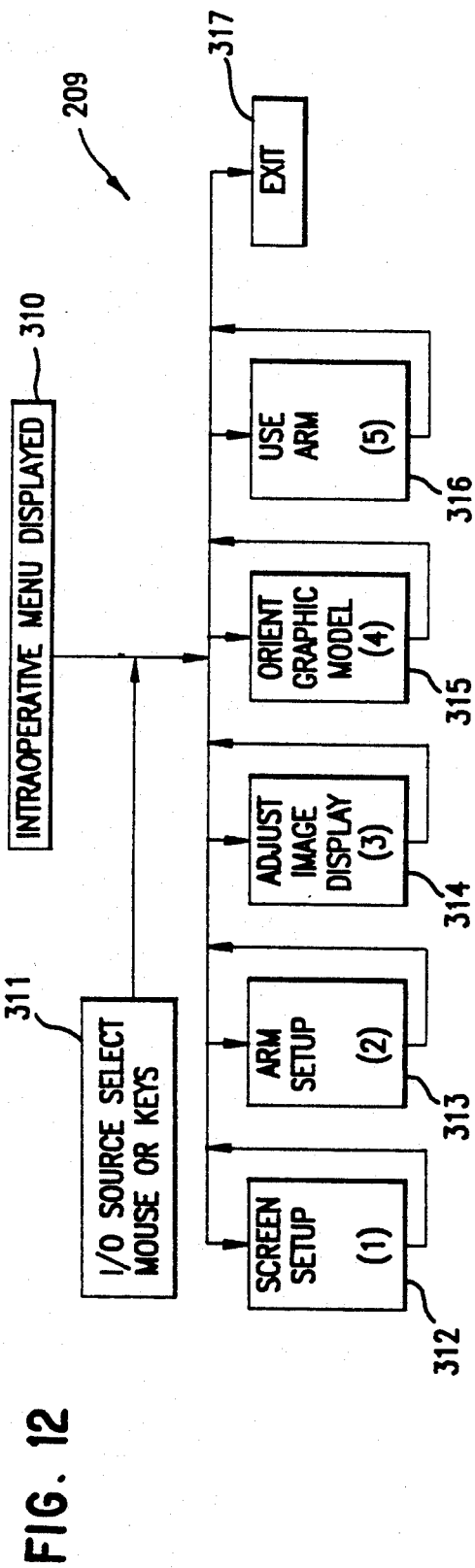
FIG. 12 is a flow chart showing the selection of functions in the intra-operative software.

The flow charts for the intraoperative software 209 are illustrated in FIGS. 12-16. The overall flow chart of the intraoperative software 209 is shown in FIG. 12. The first step is the displaying of the intraoperative menu in step 310. The I/O source is selected in step 311. Five different functions of the intraoperative menu can be selected. The first function is the screen setup 312, the second is the arm setup 313, the third is the adjust image display function 314, the fourth is the graphic model orientation 315, and the fifth is the use arm function 316. The intraoperative software is exited in step 317.

Figure 13:
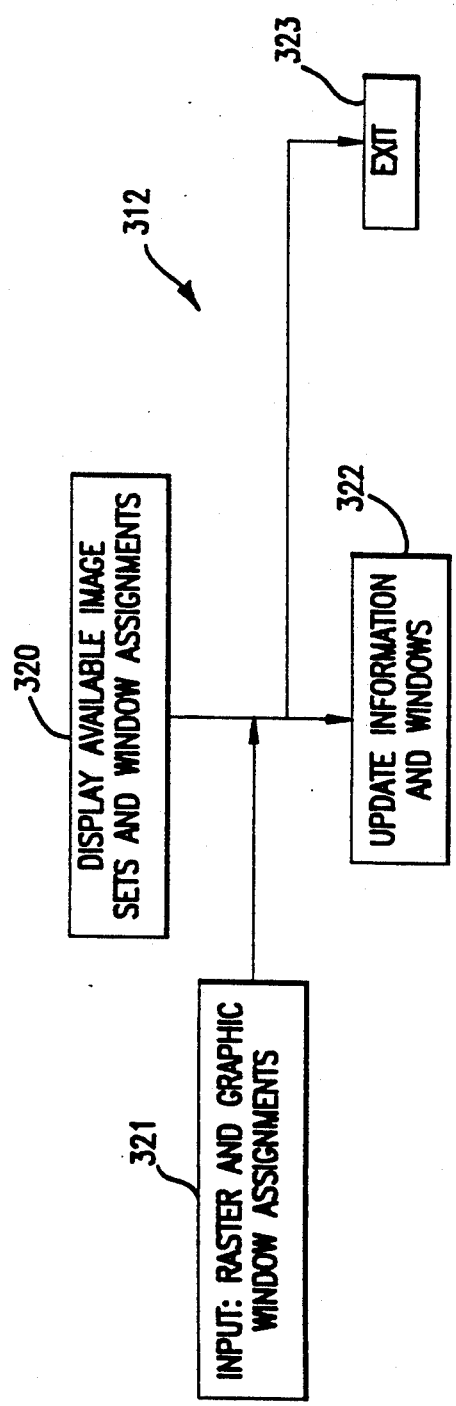
FIG. 13 is a flow chart of the first function in the intra-operative software.

FIG. 13 shows the first of the intraoperative software functions, the screen set up 312. The first step 320 is the displaying of the available image sets and window assignments. Raster and graphic window assignments are input in step 321. From here, the information in the windows are updated or the screen set of function 312 is exited in step 323.

Figure 14:
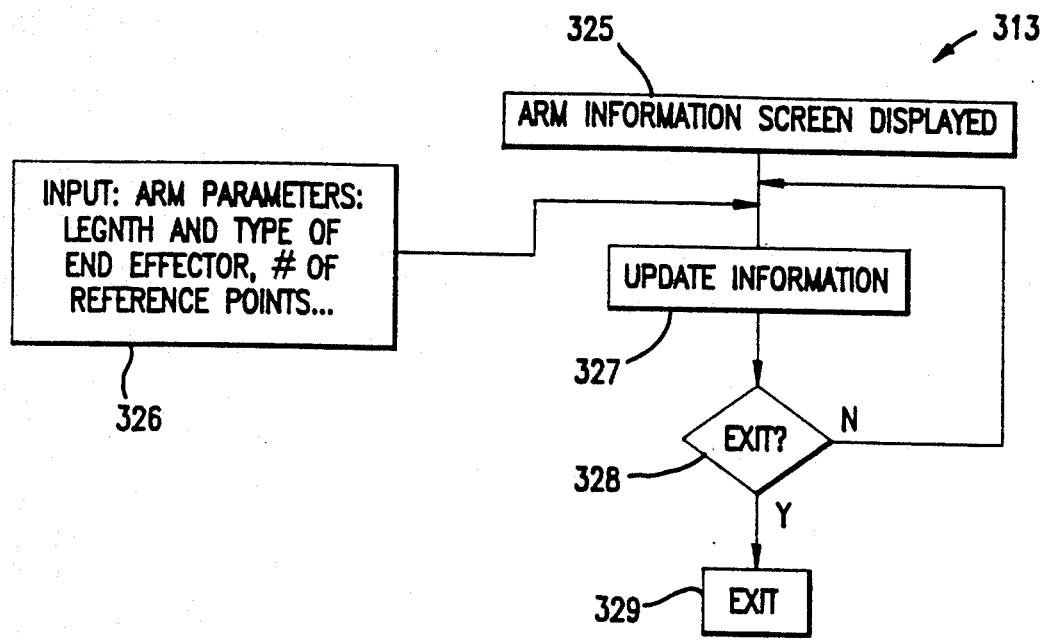
FIG. 14 is a flow chart of the second function of the intra-operative software.

FIG. 14 is a flow chart showing the second function, the arm set up 313. In step 325, the arm information screen is displayed on display 108. Arm parameters, including the length and type of surgical tool, the number of reference points, etc. are input in step 326. Information is updated in step 327 and a decision is made to exit in decision step 328. If it is decided not to exit, the software loops back to the input of the update information step 327. Otherwise, the second function 313 is exited in step 329.

The flow chart for the third function, the adjust image display function 314, is the same as that of FIG. 9

Figure 15:
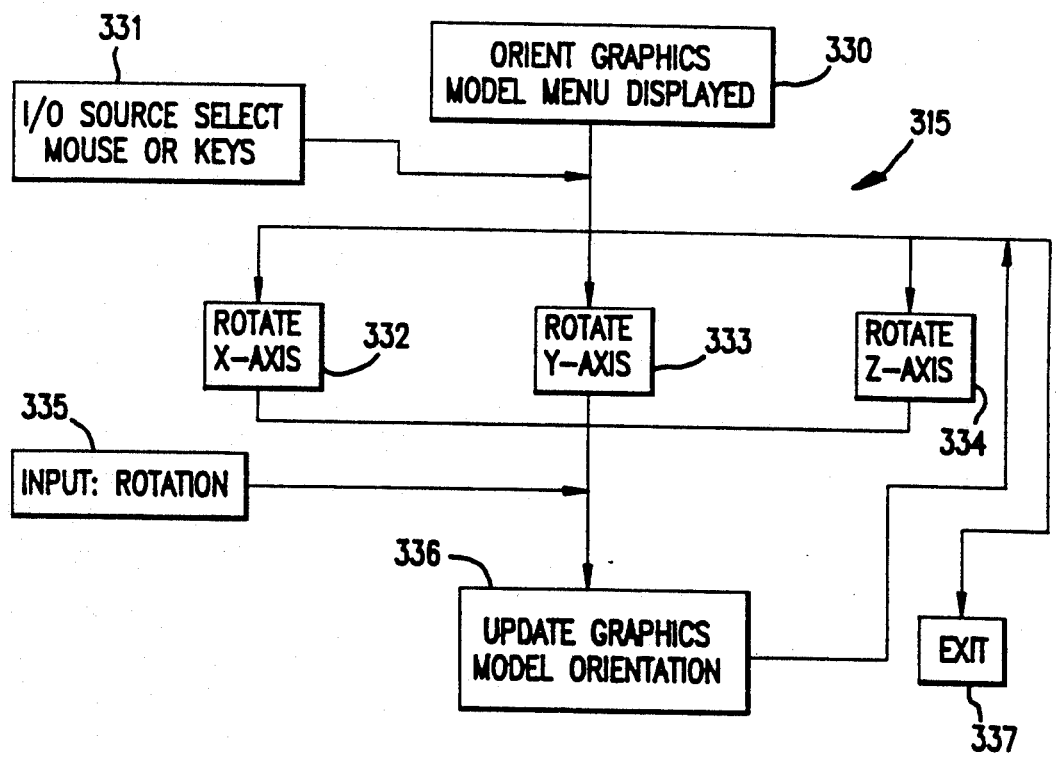
FIG. 15 is a flow chart of the fourth function of the intra-operative software.

The flow chart of FIG. 15 shows the fourth function, the adjust image display function 315. In the first step 330, the menu for this function, the orient graphics model menu is displayed. The I/O source is selected in step 331. The selection of the axis to be rotated is then made, with any of the X,Y,Z axes being able to be rotated in steps 332,333,334. The amount of rotation is input in steps 335 and a graphics model orientation is updated in step 336. From the display of the menu in display 108, the orient graphics model function 314 is exited in step 337

Figure 16:
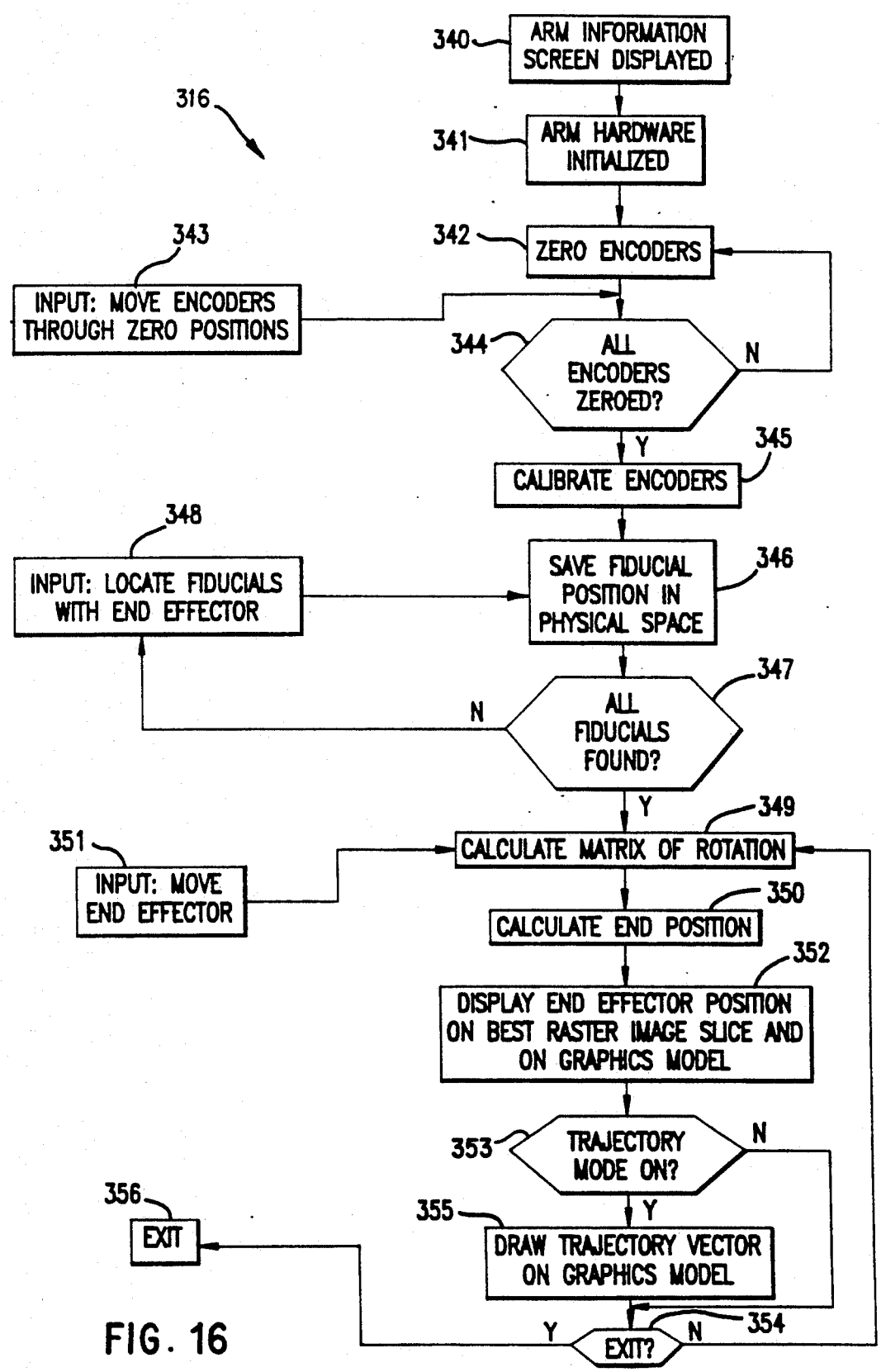
FIG. 16 is a flow chart of the fifth function of the intra-operative software.

The flow chart of FIG. 16 describes the use arm function 316. The first step is the displaying of the arm information screen 340. The arm hardware is initialized in step 341. The encoders are zeroed in step 342. The encoders are moved to their zero positions and this is input in step 343. In decision step 344, it is determined whether all the encoders are zeroed, with the negative result looping back to step 342. If all the encoders are zeroed, step 345 is performed to calibrate the encoders. The position of the fiducial implants in physical space, i.e. in the internal coordinate system, are saved in step 346. In decision step 347, it is determined whether all the fiducial implants 10A-C are located. If they are not, the fiducials are located with the tool 38 and this information is input in step 348.

When all the fiducial implants 10A-C are found, the matrix of rotation is calculated in step 349. The position of the end tip 39 of the tool 38 is calculated in step 350. An input to the step 349 (the calculation of the matrix of rotation) is provided in step 351 in which the tool 38 is moved. After the position of the end tip 39 is calculated in step 350, the position of the tool 8 is displayed on the best raster image slice and on the graphics model in step 352. It is then determined in decision step 353 whether the trajectory mode is on or not. If it is not, it is determined in decision step 354 whether or not to exit the function 316. If the trajectory mode is on, a trajectory vector is drawn on the graphics model in step 355. Once the trajectory vector on the graphics model is drawn, it is then determined once again whether or not to exit the function 316. If it is decided to exit, exit step 356 is then executed. If not, the program loops back to step 349 to calculate a matrix of rotation.

The above-described flow charts in FIGS. 5-16 describe an embodiment of software which can be used in the present invention. However, other embodiments of the program to use the arm 34 of the present invention are contemplated. Further, although the invention 34 has been described as being used with fiducial implants 10A-C, the arm 34 can also be used with any system in which internal points of reference are provided.

What is claimed is:

1. An interactive system guiding the use of a surgical tool using an imaging technique, comprising:
    an imaging device generating image data of a patient's anatomy, said image data being defined with respect to an image coordinate system;
    a surgical tool;
    a mechanical arm having a fixed base at a first end and a tool holder that holds the surgical tool at a second end;
    means for displaying at least one graphical representation of image data of and patient's anatomy, said means including a display screen;
    a computer means coupled to the means for displaying and to the mechanical arm for tracking the location of the surgical tool through a physical coordinate system, for relating said physical coordinate system to the image coordinate system, and for causing said display means to display graphical representations of image data corresponding to the location of the surgical tool within the image coordinate system;
    said computer means having a local data base storing patient identification information and corresponding image data and image coordinate system;
    means for determining whether particular patient identification information is in the local data base;
    said display means displaying patient identification information on said display screen;
    means for defining a desired orientation for said image data and image coordinate system in said local data base corresponding to said patient identification information;
    means for reformatting said image data to said desired orientation and
    means for generating a graphic representation of the reformatted image data of a surgical volume of interest, said graphic representation capable of being displayed on said display screen.

2. The system of claim 1, wherein said mechanical arm has joints and degrees of freedom of motion and means for electrically encoding movement of said joints relative to said base, said means for encoding being coupled to said computer means to provide said computer means with the electrically encoded movements of said joints.

3. The system of claim 2, wherein the means for electrically encoding movement of said joints are optical encoders.

4. The system of claim 3, wherein one optical encoder is provided for each degree of freedom of said mechanical arm.

5. The system of claim 1, wherein said means for displaying said image from an image space includes displaying a raster image.

6. The system of claim 1, wherein said means for displaying includes displaying a plurality of images with the images being provided by different imaging techniques.

7. The system according to claim 1 further comprising means for editing the graphic representation.

8. The system according to claim 1 further comprising means for marking regions of interest on the images.

9. The system according to claim 1 wherein the mechanical arm has a number of degrees of freedom, and the system further comprises:
 means for confirming patient data;
 means for setting up the computer means and surgical tool for a specific surgical procedure;
 means for checking a plurality of optical encoders in said mechanical arm after start up;
 means for orienting the graphic representations of said image data according to the needs of the surgeon; and
 means for calibrating the mechanical arm to determine angular errors in each degree of freedom.

10. The system according to claim 9 where in said computer means further includes:
 (a) means for sequentially locating commonality between said physical coordinate system and said image coordinate system;
 (b) means for calculating a matrix of rotation between the physical coordinate system and the image coordinate system; and
 (c) means for transforming the position of the surgical tool in said physical coordinate system to an equivalent position in said image coordinate system.

11. The system according to claim 10 further comprising means for displaying the trajectory of the tool.

12. The system according to claim 11 further comprising means for displaying the position of the tool in image coordinate system on raster windows and in a graphic window.

13. A method of performing a surgical procedure comprising:
 scanning a portion of a patient's anatomy using an imaging technique to form image data;
 determining whether particular patient identification information is in a local data base;
 displaying patient identification information on a computer screen integrated with a computer through which the local data base can be accessed;
 defining a desired orientation for said image data
 reformatting and image data selected from the scan of the patient to said desired orientation to depict a surgical volume of interest;
 generating a graphic representation of the reformatted image data to display on said computer screen;
 locating an internal point of reference within the patient's anatomy using the image data of the scanning step;
 initializing an end tip of a surgical tool on a manipulable articulated arm by placing said end tip in a known relationship with said internal point of reference and noting said initializing in said computer;
 tracking movement in said computer of the end tip of the surgical tool through physical space that is defined with respect to a physical coordinate system; and
 displaying in real time a location of the end tip of the surgical tool with respect to the image data of said scanning step.

14. The method of claim 13, further comprising implanting fiducial implants in the patient's anatomy to serve as points of reference.

15. The method of claim 14, wherein the tracking step includes encoding the movements of joints in the arm and sending the encoded movements to the computer.

16. The method of claim 15, further comprising establishing an internal coordinate system based on the fiducial implants.

17. The method of claim 16, further comprising establishing an external coordinate system related to a fixed base of said arm, the position in space of said base being stored upon the initializing of said end tip.

18. The method of claim 17, further comprising scanning the portion of the of the patient's anatomy using a plurality of imaging techniques.

19. The method of claim 18, further comprising simultaneously displaying images from each of the plurality of imaging techniques.

20. The method of claim 19, further comprising replacing the surgical tool on said arm with a different type of surgical tool.

21. The method according to claim 13 wherein the mechanical arm has a number of degrees of freedom, said method further includes the steps of:
 confirming patient data;
 setting up said computer and said surgical tool for a specific surgical procedure;
 checking a plurality of optical encoders in said mechanical arm after start up;
 orienting the graphic representations of said image data according to the needs of the surgeon; and
 calibrating the device to determine angular errors in each degree of freedom.

22. The method according to claim 21 wherein said method further includes the steps of:
 (a) sequentially locating commonality between said physical coordinate system and said image coordinate system;
 (b) calculating the matrix of rotation between the physical coordinate system and the image coordinate system; and
 (c) transforming the position of the surgical tool in physical space to an equivalent position in said image coordinate system.

23. The method according to claim 22 further comprising displaying the trajectory of the tool.

24. The method according to claim 23 further comprising displaying the position of the tool in image coordinate system on all raster windows and in a graphic window.

* * * * *

UNITED STATES PATENT AND TRADEMARK OFFICE
CERTIFICATE OF CORRECTION

PATENT NO.  : 5,230,338
DATED       : July 27, 1993
INVENTOR(S) : George S. Allen et al.

It is certified that error appears in the above-indentified patent and that said Letters Patent is hereby corrected as shown below:

| Column | Line | |
|--------|------|---|
| 1  | 11 | Change "4,881,579" to --4,991,579--. |
| 4  | 17 | Change "11?" to --110--. |
| 4  | 66 | Change "10" to --108--. |
| 9  | 57 | Change "8" to --38--. |
| 10 | 20 | Change "and" to --said--. |
| 10 | 44 | After "orientation" insert --;--. |
| 10 | 63 | Change "space" to --coordinate system--. |

Signed and Sealed this

Eighteenth Day of October, 1994

Attest:

BRUCE LEHMAN

Attesting Officer

Commissioner of Patents and Trademarks